United States Patent
Op De Beek et al.

(10) Patent No.: US 6,788,759 B2
(45) Date of Patent: Sep. 7, 2004

(54) X-RAY EXAMINATION APPARATUS FOR RECONSTRUCTING A THREE-DIMENSIONAL DATA SET FROM PROJECTION IMAGES

(75) Inventors: Johannes Catharina Antonius Op De Beek, Eindhoven (NL); Reiner Koppe, Hamburg (DE); Erhard Paul Artur Klotz, Nuemuenster (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 72 days.

(21) Appl. No.: 10/215,715

(22) Filed: Aug. 9, 2002

(65) Prior Publication Data

US 2003/0043960 A1 Mar. 6, 2003

(30) Foreign Application Priority Data

Aug. 10, 2001 (EP) ............................................ 01203082

(51) Int. Cl.$^7$ ................................................ A61B 6/03
(52) U.S. Cl. ............................ 378/19; 378/8; 378/901
(58) Field of Search ........................... 378/4, 8, 15, 19, 378/20, 901

(56) References Cited

U.S. PATENT DOCUMENTS

| 5,333,107 A | 7/1994 | Grangeat et al. |
| 5,444,792 A | 8/1995 | Grangeat et al. |
| 5,682,413 A | 10/1997 | Wong et al. |
| 5,852,646 A | 12/1998 | Klotz et al. |
| 5,889,525 A | 3/1999 | De Murcia et al. |
| 6,320,928 B1 * | 11/2001 | Vaillant et al. ................ 378/4 |
| 2002/0049378 A1 * | 4/2002 | Grzeszczuk et al. ........ 600/427 |
| 2002/0075994 A1 * | 6/2002 | Shahidi et al. ................ 378/62 |

FOREIGN PATENT DOCUMENTS

WO   WO 00/75872 A1   12/2000

* cited by examiner

*Primary Examiner*—David V Bruce

(57) ABSTRACT

An X-ray examination apparatus includes an X-ray source and an X-ray detector and is arranged to provide a series of projection images at respective orientations of the X-ray source (1) and the X-ray detector (2) relative to a predetermined frame of reference. The orientations of the projection images are calibrated relative to this frame of reference. A basic three-dimensional data set (23) is reconstructed from the projection images. A number of directions of observations ($12_1$–$12_3$) are calibrated relative to the same frame of reference. One or more additional X-ray images ($11_1$–$11_3$) are formed for the calibrated directions of observation, that is, preferably at successive instants in time. A dynamic series of three-dimensional data sets is formed by updating the basic three-dimensional data set by means of the additional X-ray images.

18 Claims, 2 Drawing Sheets

X-RAY EXAMINATION APPARATUS FOR RECONSTRUCTING A THREE-DIMENSIONAL DATA SET FROM PROJECTION IMAGES

BACKGROUND

The invention relates to an X-ray examination apparatus which includes an X-ray source and an X-ray detector.

A known X-ray examination apparatus is described in international application WO 00/75872. The known X-ray examination apparatus reconstructs a three-dimensional data set from the series of projection images. The projection images are acquired notably by irradiating the patient to be examined from the respective orientations while using an X-ray beam emitted by the X-ray source. The orientations at which the projection images are formed are accurately calibrated, thus enabling accurate three-dimensional reconstruction without excessive artifacts. A contrast medium is administered to the patient to be examined and the projection images are acquired when the blood vessels in the part of the anatomy to be examined are filled with contrast medium. The three-dimensional reconstruction produces a three-dimensional data set which associates data values with three-dimensional spatial positions. This data set represents the structure of the blood vessels at an instant at which the vessels are filled with the contrast medium. It has been found in practice that the diagnostic information provided by display of the three-dimensional data set is still inadequate.

SUMMARY OF THE INVENTION

The invention is arranged to form a series of projection images at respective orientations of the X-ray source and the X-ray detector relative to a predetermined frame of reference. The orientations being calibrated relative to the frame of reference, and reconstructing a basic three-dimensional data set from the series of projection images.

It is an object of the invention to provide an X-ray examination apparatus which enables the spatial image information of the three-dimensional reconstruction to be combined with image information other than that contained in the projection images used for the three-dimensional reconstruction.

This object is achieved by means of an X-ray examination apparatus in accordance with the invention in which the positions of the X-ray source and the X-ray detector relative to the frame of reference are calibrated for one or more additional directions of observation. As a result, image information available for the one or more additional observation directions can be reproduced in registration with the three-dimensional data set. The combined rendition of the three-dimensional data set and the image information associated with the one or more additional directions of observation faithfully represents the spatial aspects of the object to be examined which is represented by the projection images wherefrom the basic three-dimensional data set is reconstructed and by the image information associated with the additional direction (directions) of observation. These and other aspects of the invention will be elaborated hereinafter on the basis of the following embodiments of the invention which are defined in the dependent claims.

For example, the image information associated with the additional direction (directions) of observation is available in the form of one or more additional X-ray images. Preferably, such additional X-ray images are formed as shadow images, each of which has its own projection direction. The projection directions wherefrom the additional X-ray images are formed then constitute the additional direction (directions) of observation. The additional X-ray images and the three-dimensional basic data set are reproduced with the correct mutual relationship. For example, it is advantageous to form the series of projection images at a comparatively low energy and intensity of the X-rays and to acquire the additional X-ray images at a higher intensity and/or energy of the X-rays. The patient to be examined is thus exposed to a low X-ray dose for the acquisition of the projection images for the basic three-dimensional data set. The additional X-ray images have a low noise level and hence a high diagnostic quality. The X-ray examination apparatus in accordance with the invention enables the high diagnostic quality of the additional X-ray images to be combined with the spatial image information in the basic three-dimensional data set.

Moreover, it is also possible to reproduce, together with the basic three-dimensional data set, image information acquired before or after the projection images wherefrom the basic three-dimensional data set is reconstructed. Variations in time in the object to be examined can thus be faithfully and accurately reproduced with the spatial structure of the object. For example, favorable results are obtained for the reproduction of the process of the filling of a part of the vascular system of the patient to be examined with blood with contrast medium. Preferably, there is formed a succession of additional X-ray images which show successive phases of the filling of the vascular system with blood with contrast medium. The spatial structure of the vascular system is known from the basic three-dimensional data set and the additional X-ray images provide the dynamics of the flow of the blood through the vascular system. Because the projection directions of the additional X-ray images, that is, the additional directions of observation and the projection images for the three-dimensional data set have been calibrated relative to the same frame of reference, both types of information can be made to correspond accurately. Consequently, the dynamics of the flow of blood through the vascular system can be accurately visualized in space while a comparatively low X-ray dose suffices nevertheless.

Preferably, the basic three-dimensional data set is continuously updated on the basis of the additional X-ray images; for example, it is handy to perform an update whenever a new additional X-ray image becomes available. A dynamic series of three-dimensional data sets is thus formed, successive data sets in such a dynamic series then relate to successive phases of the filling of the blood vessels with blood with contrast medium.

Furthermore, it is advantageous to store a number of preferred additional directions of observation and/or the corresponding positions for the X-ray source and the X-ray detector in advance in a memory. This facilitates the positioning of the X-ray source and the X-ray detector for the acquisition of the additional X-ray images. When the user (users) himself (themselves) is (are) allowed to store a plurality of preferred additional directions of observation and/or the associated positions of the X-ray source and the X-ray detector, the personal preferences of the relevant user (users), for example, individual radiologists, can be taken into account.

Preferably, it is ensured that for the positioning of the X-ray source and the X-ray detector for the acquisition of the one or more additional X-ray images the X-ray source and the X-ray detector are moved from a predetermined starting position to the desired position. Consequently, the desired position for the acquisition of the additional X-ray images is always reached from the same direction. It has been found that the desired position is thus accurately reached, because inter alia mechanical hysteresis effects are avoided in particular.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DETAILED DESCRIPTION

Figure 1:
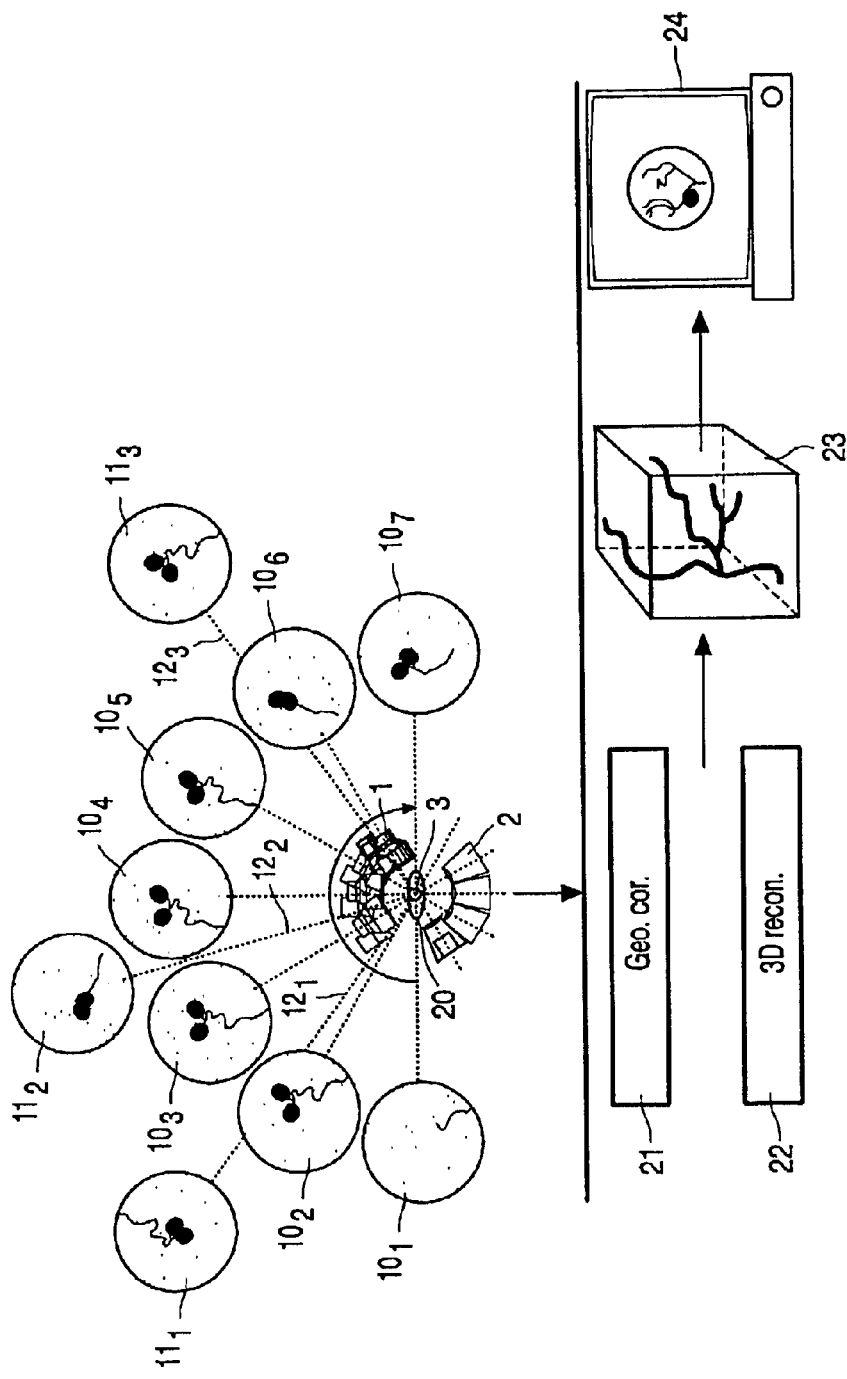
FIG. 1 is a diagrammatic representation of the 3D rotation angiography procedure in which the invention is used.

FIG. 1 is a diagrammatic representation of a set-up of the 3D rotation angiography procedure. FIG. 1 shows the X-ray source 1 and the X-ray detector 2 in a plurality of orientations relative to the patient 20 to be examined. As is indicated by the arrow, the X-ray source and the X-ray detector are rotated together around the axis of rotation 3. To this end, for example, the X-ray source and the X-ray detector are both suspended from a stand such as a C-arm 20. One of the two-dimensional projection images $10_1$–$10_7$ is formed at each of these orientations. Such projection images are often subtraction images obtained by subtracting a previously acquired mask image from an instantaneous projection image, so that the subtraction image represents practically the difference only between the instantaneous projection image and the mask image. Using a correction unit 21, a number of geometrical corrections is applied to the projection images $10_1$–$10_7$ in order to correct the projection images for known distortions, such as barrel and cushion distortion, which occur notably when an X-ray image intensifier with a television camera is used as the X-ray detector. A reconstruction unit 22 reconstructs the three-dimensional data set 23 from the projection images $10_1$–$10_7$. This three-dimensional data set is reproduced on, for example, a monitor 24 which is suitable for (quasi-) spatial display of the three-dimensional data set.

In conformity with the invention, not only the projection images $10_1$–$10_7$ are formed, but also the additional X-ray images $11_1$, $11_2$, $11_3$. The example shown utilizes three additional X-ray images. Such additional X-ray images are formed in each time one of the additional directions of observation $12_1$, $12_2$ and $12_3$. Such additional directions of observation may be situated in the plane in which the X-ray source and the X-ray detector are rotated for the acquisition of the projection images $10_1$–$10_7$; this is the case for the additional direction of observation $12_2$. Additional directions of observation may also be situated outside the plane in which the X-ray source and the X-ray detector are rotated for the acquisition of the projection images $10_1$–$10_7$; this is the case for the additional directions of observation $12_1$ and $12_3$. The additional directions of observation are defined together with the orientations of the projection images $10_1$–$10_7$, for example, relative to the calibration phantom 6 in the same position as during the calibration of the orientations of the projection images for the 3D data set. The frame of reference for the calibration of the orientations for the projection images and for the calibration of the additional directions of observation is defined by the calibration phantom in the position in which it is arranged for the calibration.

Figure 2:
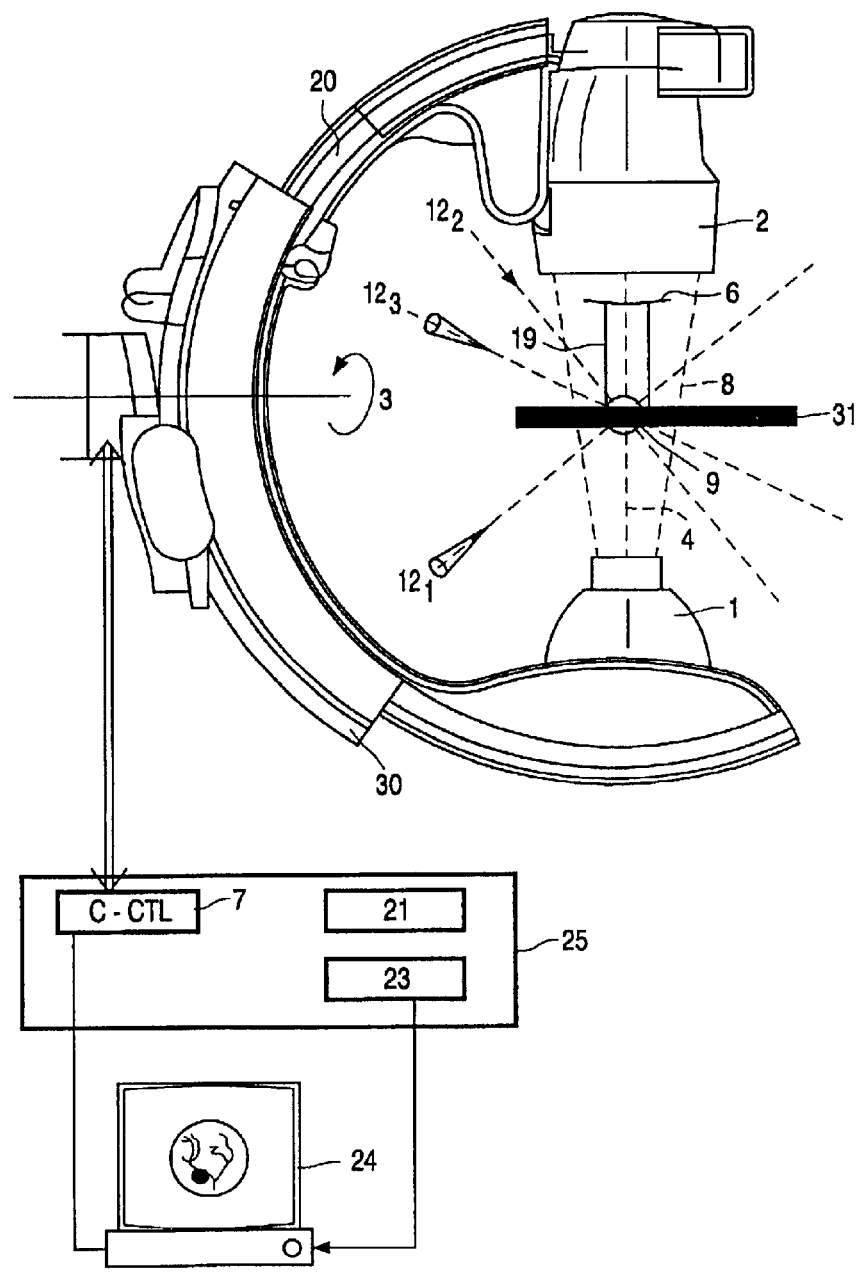
FIG. 2 is a diagrammatic representation of an X-ray examination apparatus in which the invention is used.

FIG. 2 is a diagrammatic representation of an X-ray examination apparatus in which the invention is used. The X-ray source 1 and the X-ray detector 2, in this case being constructed as an X-ray image intensifier, are suspended from a stand which is in this case a C-arm 20. The C-arm 20 is movable through a sleeve 30, the X-ray source 1 and the X-ray detector 2 then rotating together in the plane of drawing. This motion is also referred to as a rolling rotation. The sleeve 30 is also rotatable about the axis of rotation 3, the X-ray source and the X-ray detector 2 then rotating transversely of the plane of drawing; the latter rotation is also referred to as a "propeller motion". This propeller motion enables, notably in the case of cardiology, a three-dimensional reconstruction of high diagnostic quality of the heart of the patient to be examined.

In a preferred version of the calibration, the calibration phantom 6 is arranged on the tower 19. The tower 19 is placed on the patient table 31. The calibration phantom is thus situated outside the isocenter 9 and close to the X-ray image intensifier 2 in the situation shown. Under the control of the calibration control unit 7 there is formed an X-ray image, that is, the first calibration image of the calibration phantom. Subsequently, the C-arm 20 is rotated through 180° about the axis of rotation 3, that is, again under the control of the calibration unit 7; the positions of the X-ray source 1 and the X-ray detector are thus interchanged and the calibration phantom 6 is situated nearer to the X-ray source than to the isocenter 9. Under the control of the calibration control unit 7 a further X-ray image is formed of the phantom, that is, the second calibration image. By comparison of the two calibration images so as to detect a relative shift of the image of the calibration phantom, it can be checked whether the central beam line 4 extends accurately perpendicularly to the axis of rotation 3. This can be done by the naked eye by displaying both calibration images on the monitor 24. Subsequently, the orientations of the X-ray source and the X-ray detector are determined in the positions in which the projection images $10_1$–$10_7$ are accurately perpendicular to the central beam line. In the present example only seven orientations are shown for the projection images, but in practice often tens of orientations or even one hundred or more orientations are used for the projection images. In the case of such a large number it is handy to determine the orientations of the individual projection images relative to the calibrated central axis 4 on the basis of the time during which the C-arm has rotated as from a preselected starting position. This is because it has been found that the mechanical movement of the C-arm is accurately reproducible. Moreover, the additional directions of observation for the additional X-ray images $12_1$–$12_3$ are accurately determined relative to the central beam line. These additional directions of observation correspond to the projection directions $12_1$, $12_2$, $12_3$ wherefrom the patient to be examined is irradiated by means of the X-ray source in order to form the additional X-ray images. The additional directions of observation $12_1$ and $12_3$ are not situated in the plane of drawing in FIG. 2 and are reached by rotation about the axis of rotation 3. The additional direction of observation $12_2$ is situated in the plane of drawing and is reached by rotating the C-arm through the sleeve 30. Evidently, it is also possible to use additional directions of observation which are reached by combinations of movement through the sleeve 30, rotation around the axis 3 and also rotation around the central beam line 4. The rotation around the central beam line becomes possible by mounting the assembly formed by the sleeve and the C-arm 20 on a support (not shown) which is suspended from the ceiling so as to be rotatable or is mounted so as to be rotatable on a base (not shown) on the floor.

In a contemporary X-ray examination apparatus the calibration control unit 7 and the correction unit 21 with the reconstruction unit 21 are usually incorporated in a programmable processor 25. For example, the result of the calibration, the zero-point orientation, can be stored in a memory of, for example, the calibration control unit. The zero-point orientation can thus be readily fetched again.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. An X-ray examination apparatus comprising:
    a first X-ray means for forming a series of initial projection images at respective intial orientations of a first X-ray source and a first X-ray detector relative to a predetermined frame of reference;
    a means for calibrating the initial orientatins relative to the frame of reference;
    a second radiation means for forming additional projection images at additional orientations of a second radiation source and a second radiation detector;
    a means for calibrating the additional orientations relative to the frame of reference; and
    a means for reconstructing three-dimensional data sets from the initial and additional projection images.

2. The X-ray examination apparatus of claim 1 including means for forming the projection images at successive orientations at successive instants, and means for calibrating the successive orientations with the successive instants.

3. The X-ray examination apparatus of claim 1 including a means for forming separate series of projection images for separate sets of orientations relative to the frame of reference, wherein respective orientations in individual sets deviate from one another by a rotation about same axis of rotation.

4. The apparatus of claim 2, wherein the first X-ray means uses lower power X-rays than the second radiation means which uses higher power X-rays.

5. An X-ray examination apparatus including:
    an X-ray source and an X-ray detector;
    a means for moving the X-ray source and the detector through (a) a series of original directions of observation around an initial reference plane, and (b) an additional series of additional directions of observation rotated from the initial reference plane; and
    a processor programmed to;
        form a series of original projection images at the original directions of observation,
        calibrate the original projection images to a frame of reference,
        form one of more additional X-ray images for one or more additional directions of observation,
        calibrate the additional X-ray images to the frame of reference, and
        reconstruct a three dimensional data set from the original and additinal images.

6. The X-ray examination apparatus of claim 5, wherein the processor is further programmed to:
    reconstruct a dynamic series of three-dimensional data sets by updating the three-dimensional data set with respective additional X-ray images.

7. The X-ray examination apparatus of claim 5 including a means for moving at least one of the X-ray source and the X-ray detector from a predetermined starting position into a desired position to form the additional images.

8. An imaging apparatus including:
    a means for forming a series of projection images at respective orientations relative to a predetermined frame of reference;
    a means for calibrating the orientations relative to the frame of reference;
    a means for forming separate series of projection images for separate sets of orientations relative to the frame of reference, which orientations for individual sets of orientations deviate from one another by a rotation about an axis of rotation which is specific of the individual sets; and
    a means for reconstructing a three-dimensional data set from the projection images.

9. The X-ray examination apparatus of claim 8 wherein the respective specific axes of rotation have been rotated relative to an axis of revolution.

10. A method of X-ray examination comprising the steps of:
    irradiating a subject with an x-ray source;
    detecting the radiation with a detector;
    forming a series of original projection images at respective original orientations of the X-ray source and the X-ray detector relative to a predetermined frame of reference, which original orientations are situated in a single rotation plane;
    calibrating the original orientations relative to the frame of reference;
    forming additional X-ray images for additional directions of observation which are rotated from the single rotation plane;
    calibrating the additional directions of observation relative to the frame of reference; and
    reconstructing a three-dimensional data set from the original and additional projection images.

11. The method of X-ray examination of claim 10 including the step of forming separate series of projection images for separate sets of orientations of the X-ray source and the X-ray detector relative to the frame of reference wherein respective orientations in individual sets deviate from one another by a rotation about same axis of rotation.

12. The method of X-ray examination of claim 10, wherein the step of reconstructing further includes:

reconstructing a dynamic series of three-dimensional data sets by dynamically updating the three-dimensional data set with respective additional X-ray images.

13. The method of X-ray examination of claim 10 including the steps of forming the projection images at successive orientations at successive instants and calibrating the successive orientations with the successive instants.

14. The method of X-ray examination of claim 10 including:

reaching the additional directions of observation by adjusting at least one of a position of the X-ray source and a position of the X-ray detector from a predetermined position.

15. An imaging apparatus including:

a means for forming original and additional projection images at respective original and additional orientations relative to a predetermined frame of reference;

a means for calibrating the original and additional orientations relative to the frame of reference; and a means for reconstructing a dynamic series of three-dimensional data sets including:
a means for reconstructing a basic three-dimensional data set from the original projection images, and
a means for dynamically updating the basic three-dimensional data set with the successive additional images.

16. An imaging method including:

forming original and additional projection images at respective original and additional orientations relative to a predetermined frame of reference;

calibrating the original and additional orientations relative to the frame of reference; and reconstructing a dynamic series of three-dimensional data sets including:
reconstructing a basic three-dimensional data set from the original projection images, and
updating the basic three-dimensional data set with successive additional images.

17. The imaging method including:

forming a series of projection images at respective orientations relative to a predetermined frame of reference;

calibrating the orientations relative to the frame of reference; and forming separate series of projection images for separate sets of orientations relative to the frame of reference which orientations for individual sets of orientations deviate from one another by a rotation about an axis of rotation which is specific of the individual sets.

18. The method of X-ray examination apparatus as claimed in claim 17 including rotating the respective specific axes of rotation relative to an axis of revolution.

* * * * *